(12) United States Patent
Dyer et al.

(10) Patent No.: US 8,663,068 B1
(45) Date of Patent: Mar. 4, 2014

(54) UNIVERSAL EXERCISE GUIDANCE SYSTEM

(71) Applicant: Precor Incorporated, Woodinville, WA (US)

(72) Inventors: David E. Dyer, Renton, WA (US); James S. Birrell, Seattle, WA (US); Brady A. Olason, Mukilteo, WA (US); Brian D. Wilson, Bothell, WA (US); David W. Flynt, Lake Forest Park, WA (US); Autumn L. Stroupe, Kirkland, WA (US)

(73) Assignee: Precor Incorporated, Woodinville, WA (US)

( * ) Notice: Subject to any disclaimer, the term of this patent is extended or adjusted under 35 U.S.C. 154(b) by 0 days.

(21) Appl. No.: 14/082,766

(22) Filed: Nov. 18, 2013

Related U.S. Application Data

(63) Continuation of application No. 12/888,638, filed on Sep. 23, 2010, now Pat. No. 8,613,689.

(51) Int. Cl.
*A63B 24/00* (2006.01)

(52) U.S. Cl.
USPC .............. 482/8; 482/1; 482/9; 482/901

(58) Field of Classification Search
USPC ............. 482/1–9, 900–902; 434/247
See application file for complete search history.

(56) References Cited

U.S. PATENT DOCUMENTS

| | | | | |
|---|---|---|---|---|
| 5,362,069 | A * | 11/1994 | Hall-Tipping | 463/7 |
| 8,287,434 | B2 * | 10/2012 | Zavadsky et al. | 482/5 |
| 2007/0287597 | A1 * | 12/2007 | Cameron | 482/8 |
| 2009/0138488 | A1 * | 5/2009 | Shea | 707/10 |

* cited by examiner

*Primary Examiner* — Glenn Richman
(74) *Attorney, Agent, or Firm* — Terence P. O'Brien; Todd A. Rathe

(57) ABSTRACT

An exercise guidance system displays either a workout option or different exercise options based on a person's exercise objectives. In one embodiment, the displayed option or options is additionally based at least partially upon a metabolic equivalent. In another embodiment, the displayed option or options is additionally based at least partially upon the time current available time for the workout.

26 Claims, 5 Drawing Sheets

WORKOUT 220

| EXERCISE OPTIONS | | PARAMETERS |
|---|---|---|
| OPTION 300 | ◯1 | $P_{1,1}$ |
| OPTION 302 | ◯1 | $P_{1,2}$ |
| OPTION 304 | ◯1 | $P_{1,3}$ |
| OPTION 306 | ◯2 | $P_{2,1}$ |
| OPTION 308 | ◯2 | $P_{2,2}$ |
| OPTION 310 | ◯3 | $P_{3,1}$ |
| OPTION 312 | ◯3 | $P_{3,2}$ |
| | | |
| OPTION 314 | ◯1 | $P_{1,4}$ |
| + | ◯4 | $P_{4,1}$ |
| | | |
| OPTION 316 | ◯2 | $P_{2,1}$ |
| + | ◯4 | $P_{4,2}$ |
| | | |
| OPTION 318+ | ◯3 | $P_{3,1}$ |
| + | ◯2 | $P_{2,3}$ |
| + | ◯4 | $P_{4,3}$ |

FIG. 6

UNIVERSAL EXERCISE GUIDANCE SYSTEM

CROSS-REFERENCE TO RELATED PATENT APPLICATIONS

The present application is a continuation of co-pending application Ser. No. 12/888,638 filed on Sep. 23, 2010 by Dyer et al. and entitled UNIVERSAL GUIDANCE SYSTEM, the full disclosure of which is hereby incorporated by reference.

The present application is related to U.S. Pat. No. 7,955,219 issued on Jun. 7, 2011 to James S. Birrell, Brady A. Olason, David W. Flynt, Autumn L. Stroupe and David E. Dyer and entitled EXERCISE COMMUNITY SYSTEM, the full disclosure of which is hereby incorporated by reference. The present application is related to co-pending application Ser. No. 12/572,448 filed on Oct. 2, 2009 by David E. Dyer, James S. Birrell, Brady A. Olason, Brian D. Wilson, David W. Flynt and Autumn L. Stroupe and entitled EXERCISE GUIDANCE SYSTEM, the full disclosure of which is hereby incorporated by reference.

BACKGROUND

Individuals often seek to attain fitness goals. However, maintaining disciplined work out regimens is often difficult due to sickness, work interruptions and various other changes in circumstance. In addition, exercise plans or routes for meeting fitness goals are often inflexible, limiting the individual to use of a designated form of exercise on a particular exercise machine. Such plans do not provide an individual with choices, leading the plan becoming stale and the individual losing interest. As a result, the fitness goals of an individual are often difficult to reach.

BRIEF DESCRIPTION OF THE DRAWINGS

FIG. 6 illustrates a display of workout options presented by the exercise guidance system of FIG. 1.

DETAILED DESCRIPTION OF THE EXAMPLE EMBODIMENTS

Figure 1:
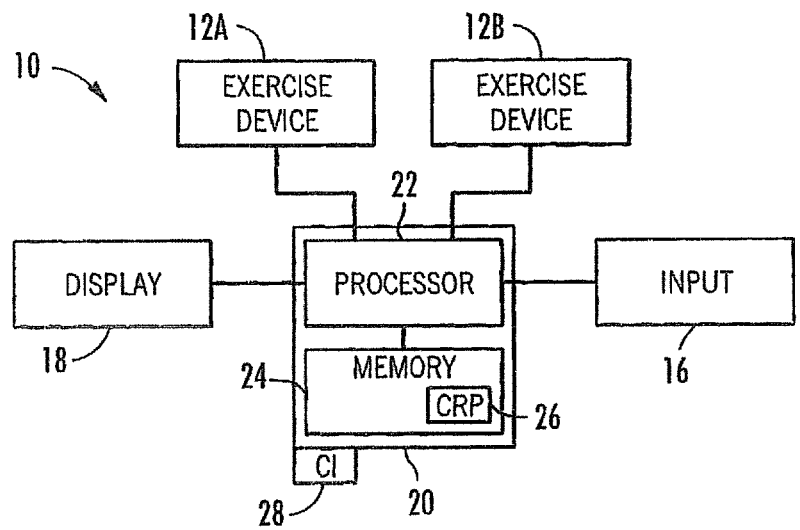
FIG. 1 is a schematic illustration of an exercise guidance system according to an example embodiment.

FIG. 1 schematically illustrates exercise guidance system 10 according to an example embodiment. As will be described hereafter, exercise guidance system 10 identifies an exercise route for achieving one of more fitness objectives or goals using one or more exercise devices and automatically adjusts the route based upon a comparison of exercise results or exercise metrics with the exercise route, user adherence and unplanned or planned user events. As a result, exercise guidance system 10 takes into account interruptions or breaks in an exercise regimen such as sickness, travel, work or life changes interruptions, goal realignment and other changes in circumstances. For purposes of this disclosure, the term "exercise route" shall mean a plan, specification, path, recipe or other step by step directions or instructions for using one or more exercise activities to make progress towards a fitness or other exercise objective.

Exercise guidance system 10 includes a plurality of fitness equipment units or exercise devices 12A, 12B (collectively referred to as exercise devices 12), input 16, display 18 and controller 20. Exercise devices 12 comprise exercise machines by which an individual may exercise by applying force or motion to one or movable structures associated with exercise device 12. Exercise devices 12 are configured to sense or measure one or more attributes of an individual such as body weight, body composition and heart rate, as well as a means of collecting subjective user input. Exercise devices 12 are further configured to sense exercise results comprising the power, force or motion applied by the individual exercising such as the rate at which foot supports or swing arms are driven, the rate and incline which a treadmill is driven, the cadence of the user, and the like. The individual attributes sensed by exercise device 12 as well as the exercise results are communicated to controller 20.

In one embodiment, exercise devices 12 communicate with controller 20 in a wired fashion. In another embodiment, exercise devices 12 communicate with controller 20 in a wireless fashion. In one embodiment, exercise device 12 may communicate with controller 20 using a local area network or communicate using Internet communication. In embodiments where system 10 includes a single exercise device 12 and wherein controller 20 is incorporated as part of the single exercise device, such communication may be made directly in a wired or wireless fashion, or other transferable means such as USB flash drives.

Figure 2:
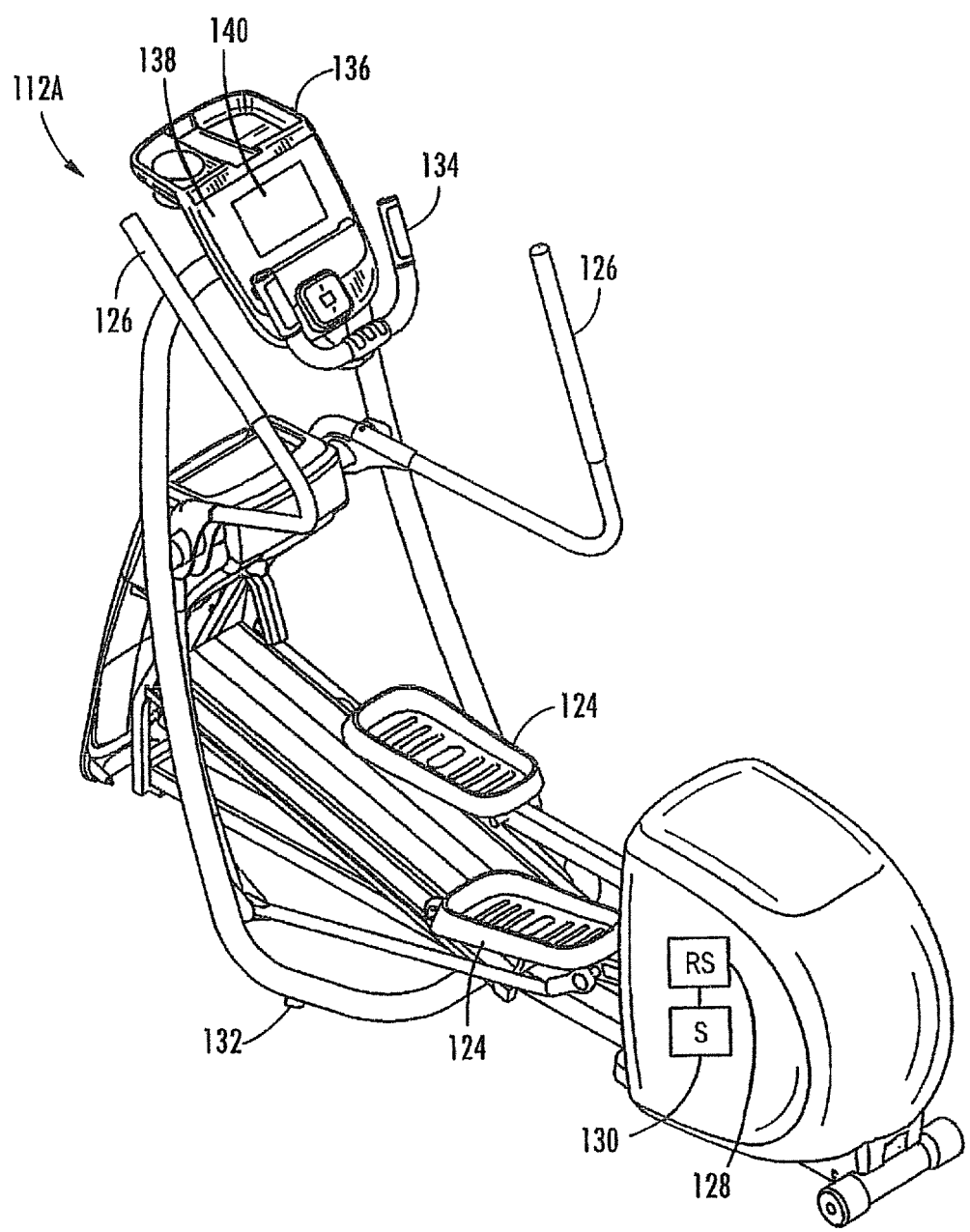
FIG. 2 is a rear perspective view of one example of the exercise device of the system of FIG. 1.
Figure 3:
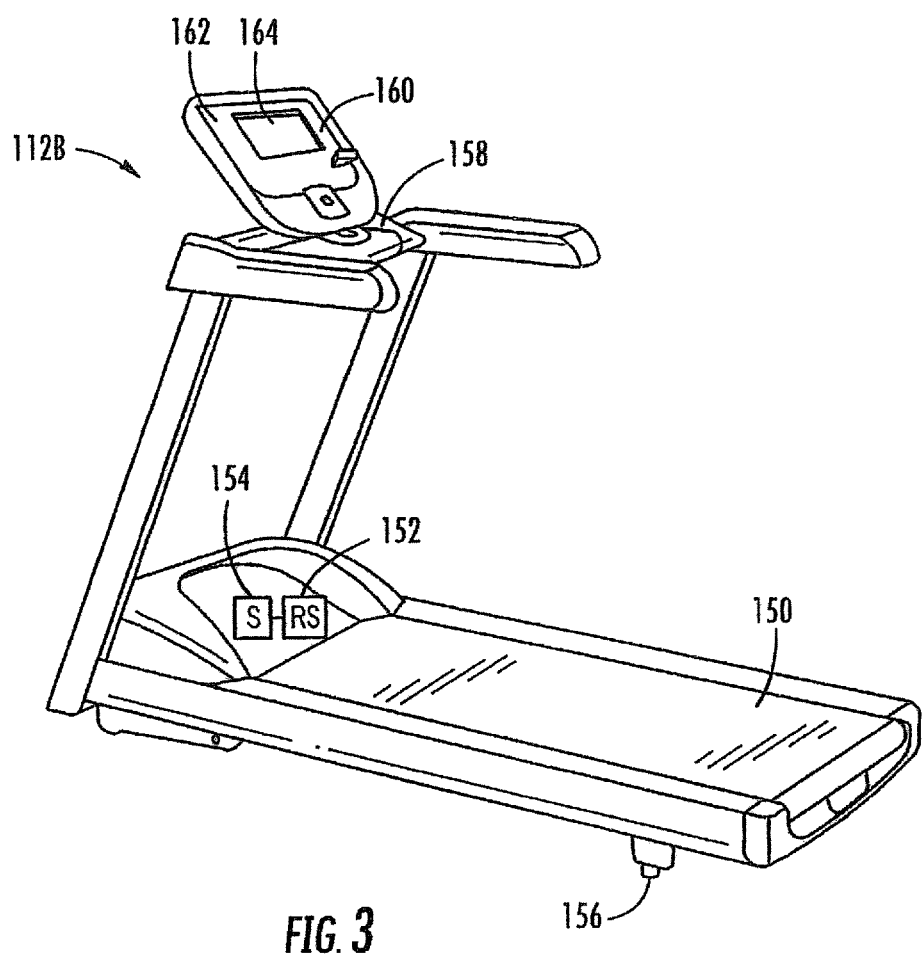
FIG. 3 is a rear perspective view of another embodiment of an exercise device of the system of FIG. 1.

FIGS. 2 and 3 illustrate exercise devices 112A and 112B, specific examples of exercise devices 12A and 12B, respectively. In one embodiment, exercise device 112A comprises an elliptical machine. The elliptical machine 112A generally includes foot supports 124, swing arms 126, one or more resistant sources 128 (schematically shown), one or more sensors 130, body weight sensor 132, body composition sensor 134 and the control panel 136. Foot supports 124 and swing arms 126 are configured to be engaged by an individual who is exercising, wherein the person exercising exerts force or motion against foot supports 124 and swing arms 126 to move such structures against a resistance provided by the one of more resistant sources 128. Resistance sources 130 resist movement of foot supports 124 and swing arms 126. In one embodiment, resistance sources 128 may comprise frictional resistance mechanisms, air brakes, Eddy current brakes, electrical generators or other devices configured to provide a controllable and adjustable resistance to such motion. In one embodiment, resistance sources 128 resist movement of foot supports 124, wherein movement of swing arms 126 is not resisted or wherein swing arms 126 are omitted. The amount or extent of resistance provided by the one of more resistant sources 128 is communicated to controller 20 (shown in FIG. 1).

Sensors 130 comprise one or more sensing devices configured to sense or detect exercise metrics or values such as the speed or rate at which foot supports 124 and potentially swing arms 126 are driven by an individual during a workout. Such sensed values are communicated to controller 20 (shown in FIG. 1). Although resistance sources 128 and sensors 130 are schematically illustrated as being located at a rear of the elliptical exercise device 112A, in other embodiments, resistance sources 128 and sensors 130 may be located at a front of exercise device 112A or at other locations.

Body weight sensor 132 comprises one or more devices configured to detect the weight of an individual. In the example illustrated, sensor 132 comprises pads or feet which sense the weight of an individual. The weight of the individual is determined by sensing the overall weight when a person has mounted exercise device 112A and subtracting the weight of exercise device 112A by itself. The detected body weight of an individual is communicated to controller 20 (shown in FIG. 1).

Sensors 134 comprise devices configured to sense a person's heart rate as well as the percent of body weight that is attributable to lean muscle mass and body fat. In the example illustrated, sensors 134 comprise handgrips configured to detect individual's heart rate as well as his or her body composition based upon an electrical resistance or in other known manners. The detected heart rate and body composition are communicated to controller 20 (shown in FIG. 1). In other embodiments, weight sensor 132 and/or heart rate-body composition sensor 134 may be omitted. For example, in other embodiments, an individual's heart rate may be detected using a chest strap or other similar sensing device. In such embodiments, the weight of an individual or his or her body composition may be entered using input 16 (shown in FIG. 1) or by a connected device such as a wireless scale.

Control panel 136 comprises that part of exercise device 112A by which an individual exercising may interact with exercise device 112A. In particular, control panel 136 facilitates the entry of commands or input of data to exercise device 112A while also providing feedback output to be person or individual exercising. Control panel 136 includes various inputs 138 and one or more displays 140. In one embodiment, one or both of inputs 138 and displays 140 may serve as the input 16 and the display 18 of FIG. 1. In other embodiments, input 16 and display 18 may be provided by other structures separate from exercise device 112A.

As shown by FIG. 3, exercise device 112B comprises an exercise device of a different type as compared to exercise device 112A. As a result, exercise device 112B provides a different type of workout. By increasing the diversity of workouts, exercise device 112 enhances the ability of a person to meet his or her fitness objectives. In the example illustrated, exercise device 112B comprises a treadmill. In other embodiments, exercise devices 112A and 112B may comprise exercise equipment other than an elliptical machine and a treadmill.

Exercise device 112B includes a treadmill belt 150, one or more resistance sources 152 (schematically shown), one of more sensors 154 (schematically shown), body weight sensors 156, heart rate/body composition sensors 158 and a control panel 160. Treadmill belt 150 is configured to be engaged by an individual who is exercising, wherein the person exercising exerts force or motion against belt 150 to move the belt 150 against a resistance provided by the one of more resistant sources 152 or is required to keep pace with the treadmill belt.

Resistance source 152 resists movement of belt 150. In one embodiment, resistance sources 152 may comprise a frictional resistance mechanism, an air brakes, an Eddy current brake, an electrical generator or other devices configured to provide a controllable and adjustable resistance to such motion. The amount or extent of resistance provided by the one of more resistance sources 152 is communicated to controller 20 (shown in FIG. 1).

Sensors 154 comprise one or more sensing devices configured to sense or detect exercise metrics or values such as the speed or rate at which belt 150 is driven by an individual during a workout. Such sensed values are communicated to controller 20 (shown in FIG. 1). Although resistance sources 152 and sensors 154 are schematically illustrated as being located at a front of the treadmill exercise device 112AB, in other embodiments, resistance sources 152 and sensors 154 may be located at a rear of exercise device 112B or at other locations.

Body weight sensor 156 comprises one or more devices configured to detect the weight or mass of an individual. In the example illustrated, sensor 156 comprises pads or feet which sense the weight of an individual. The weight of the individual is determined by sensing the overall weight when a person has mounted exercise device 112B and subtracting the weight of exercise device 112B by itself. The detected body weight of an individual is communicated to controller 20 (shown in FIG. 1). In another embodiment, the weight measuring device is a standalone but is connected to the exercise device wirelessly or in a wired manner.

Sensors 158 comprise devices configured to sense a person's heart rate as well as the percent of body weight that is attributable to lean muscle mass. In the example illustrated, sensors 158 comprise handgrips configured to detect individual's heart rate as well as his or her body composition based upon an electrical resistance or in other known manners. The detected heart rate and body composition are communicated to controller 20 (shown in FIG. 1). In other embodiments, weight sensor 156 and/or sensor 158 may be omitted. In such embodiments, the weight of an individual or his or her body composition may be entered and provided to controller 20 using input 16 (shown in FIG. 1). The person's heart rate may be sensed using other devices.

Control panel 160 comprises that part of exercise device 112B by which an individual exercising may interact with exercise device 112B. In particular, control panel 160 facilitates the entry of commands or input of data to exercise device 112B also providing feedback output to the person or individual exercising. Control panel 160 includes various inputs 162 and one or more displays 164. In one embodiment, one or both of inputs 162 and displays 164 may serve as the input 16 and the display 18 of FIG. 1. In other embodiments, input 16 and display 18 may be provided by other structures separate from exercise device 112B.

As shown by FIG. 1, input 16 comprises one or more devices by which data or information may be provided to controller 20. Input 16 enables an individual to enter his or her fitness objectives as well as other attributes such as his or her age, weight, gender, time available for workouts, frequency per week preferences, available times or days for working out or types of exercise machines to be used for achieving his or her fitness objectives. Input 16 further enables an individual to input requests or commands to controller 20. In one embodiment, input 16 comprises a keyboard, mouse, touchpad, touch screen or other input device. Input 16 may be provided as part of a control panel associated with one of exercise devices 12 or may be a separate input device such as an input device associated with another computer, personal data assistant (PDA) or the like that is in communication with controller 20.

Display 18 comprises one or more devices by which information or data may be output or presented to an individual. Display 18 enables controller 20 to provide information such as an exercise route, exercise parameters, fitness goal objective forecasts and the like. In one embodiment, display 18 may comprise a display screen. In still other embodiments, display 18 may communicate information in other manners such as through the use of light emitting diodes or audible signals such as sounds of voice communication. In one embodiment, display 18 may be provided as part of one of exercise devices 12. In yet other embodiments, display 18 may comprise a screen provided as part of other devices separate from exercise devices 12 such as a display associated with another computer, personal data assistant (PDA) or the like that is in communication with controller 20.

Controller 20 comprises one or more processing units 22 and associated memory 24 configured to provide a person or individual with guidance, motivation and inspirational messaging toward achieving his or her fitness objectives. For purposes of this application, the term "processing unit" shall mean a presently developed or future developed processing unit that executes sequences of instructions contained in a memory. Execution of the sequences of instructions causes the processing unit to perforin steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 20 may be embodied as part of one or more application-specific integrated circuits (ASICs). Unless otherwise specifically noted, the controller is not limited to any specific combination of hardware circuitry and software, nor to any particular source for the instructions executed by the processing unit.

In the example illustrated, memory 24, which provides instructions to processor 22, includes one or more computer readable programs 26. Computer readable programs 26 comprise computer readable instructions, such as software code, configured to direct the operation of the one more processors 22. The computer readable program 26 are specifically configured to direct the processor 22 to carry out functions or processes including, but not limited to, (1) receiving a fitness objectives for an individual, (2) identifying and storing an exercise route for achieving the fitness objectives of an individual using one or more of the exercise devices 12, (3) receiving exercise metrics (exercise results data) from the one of more exercise devices 12, (4) comparing the exercise metrics with the exercise route and expected results and (5) based on the comparison, adjusting the previously formed exercise route. The new adjusted exercise route, which includes prescribed workout parameters for multiple individual workouts, is then presented or otherwise displayed to the individual.

As noted above, the computer readable program 26 instructs the one or more processors 22 to receive a fitness objective for an individual. Examples of fitness objectives include, but are not limited to, weight management, fitness management, event preparation and performance enhancement. With the weight management objective, the goal is to attain or maintain the desired weight. With a fitness management objective, the goal might be to attain or maintain a certain level of fitness as measured various physiological markers such as an individual's heart rate given a predefined workout intensity, blood pressure, etc. An event preparation objective might be to prepare for a specific exercise event or competition such as a future race, bicycling event or the like. Finally, a performance enhancement objective might be to achieve or maintain a certain speed or other exercise metric on a particular exercise device or while performing a specific modality or activity.

Once a fitness objective has been received, processor 22, following instructions provided by the computer readable program 26, identifies and stores an exercise route for achieving the fitness objective using one or more of the exercise devices 12. To do so, processor 22 may provide prompts or inquiries via display 18 (as a part of the exercise device or as a separate display) requesting that the individual input certain individual attributes such as his or her age, weight, gender, time available for workouts, frequency per week preferences, preferred exercise devices the date at which the fitness objectives are to be met, and answers to other pertinent questions. Controller 20 may further request information such as the person's weight and body composition. Alternatively, this information may be obtained directly from the exercise device if equipped with such sensors.

Figure 4:
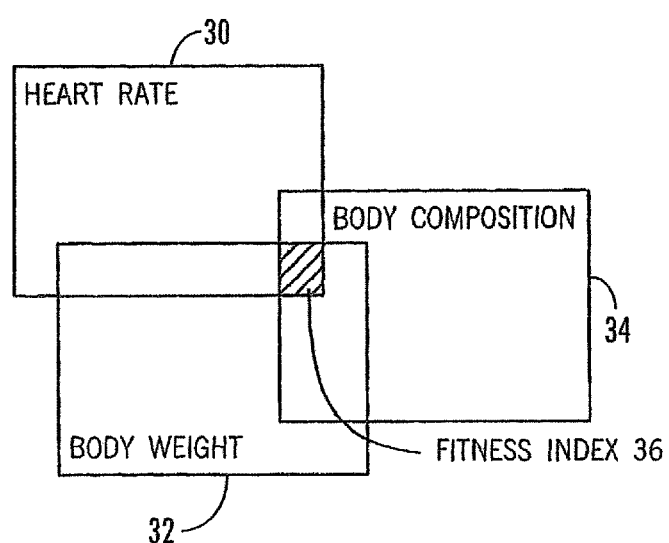
FIG. 4 is a schematic diagram illustrating the identification of a fitness index for use in the creation of an exercise route by the system of FIG. 1.

In addition to requesting the input of such information, controller 20 may also request that the individual complete a fitness evaluation test. In particular, controller 20 may display a fitness test parameter for one of exercise devices 12. Exercise parameters include, but are not limited to, a certain speed or rate for a certain duration, a certain level of resistance or a workout intensity. Alternatively, controller 20 may control the exercise device 12 being used for the test such that the noted parameters are set. During exercise by the person as part of the test, controller 20 receives fitness test metrics or the exercise results. In one embodiment, such results are in the form of a heart rate at the prescribed test intensity levels. During the test, exercise device may further detect the individual's body composition and body weight. These values are also communicated to controller 20. At the conclusion of the test workout, controller 20 may ask the individual for his or her assessment of whether the test workout was easy, moderate or hard. As schematically represented by FIG. 4, controller 20 uses each of the test results (heart rate) and sensed attributes (body weight 32 and body composition 34), controller 20 assesses a fitness level or fitness index 36 of the individual and uses the fitness level 36 to identify or create the exercise route.

In particular embodiments, controller 20 may utilize other input or historical information in forming or identifying an exercise route. For example, in one embodiment, controller 20 may additionally include a communication interface 28 by which controller 20 may communicate and receive data or input from external sources. For example, in one embodiment, controller 20 may receive input or historical data from the user, a physician, health care provider, or personal trainer (identified by the individual using input 16) via the communication interface 28. For example, when creating the exercise route, controller 20 may automatically correspond and communicate with a medical record (located at a server of a doctor or health care provider) to gain additional input. In particular embodiments, controller 20 may request authorization the input 16 to gain authorization or access to such data.

Controller 20 stores the identified or generated exercise route and presents the exercise route to the individual via display 18. The generated exercise route may be stored as part of a user profile which may be uploaded to exercise devices 12 by a USB, wireless or wired connection. In particular embodiments, controller 20 may further be configured to automatically transmit or forward the prescribed exercise route as well as exercise objectives to the physician or health care provider.

For purposes of this disclosure, the term "exercise route" means one or more prescribed workout parameters (the parameters of an individual workout) and the frequency (i.e. number of times per week) of each prescribed workout on one or more of exercise devices 12. The exercise route may include individual workout parameters, weekly groupings of workouts and collections of weekly groupings. An exercise route provides an exercise regimen for an individual. An excise route may include multiple distinct types of workouts including, but not limited to, rest (active recovery), active regeneration, lower aerobic, upper aerobic, aerobic power, anaerobic crossover, aerobic power and maximum anaerobic type workouts. In some embodiments, the individual may have the option of selecting or overriding an exercise route. In other embodiments, controller 20 may automatically adjust at least some of the settings of the exercise device to match the exercise parameters or workout parameters of the exercise route based upon where along the route the individual presently resides.

During an individual workout, controller 20 receives exercise metrics or exercise results from a particular exercise device 12. As noted above, such exercise results may include the level of resistance applied by resistance sources 128, 152 (shown in FIGS. 2 and 3) the intensity of the workout, the rate or speed at which the movable members of the exercise device are driven or moved, the duration of the workout or duration of portion or segments of the workout at different intensity levels or different settings, the sensed or detected heart rate of the individual or other metrics or values associated with the workout. During an individual workout, controller 20 may further receive updated results for the individual's body composition and body weight.

Using the received exercise results, controller 20 forms a comparison of the specific exercise results with the expected exercise results based on the recommended exercise route. Based upon this comparison, controller 20, following the instructions of computer readable program 26, adjusts the route. In one embodiment, the adjustment of the route may be further based upon additional input received via communication interface 28 from a physician, health care provider, personal trainer or other information provider.

In one embodiment, such route adjustment may be based upon a degree of compliance to the route. For example, if the individual exercising consistently produces exercise results that are substantially out of compliance and not meeting the prescribed levels of the exercise route, controller 20 may lessen the intensity and lessen the frequency of workouts. The route adjustment may result in a delayed estimated date for attaining the fitness objective. Alternatively, if the individual exercising consistently outperforms the route, controller 20 may increase the intensity, frequency or other parameters of the workouts. In one embodiment, controller 20 is configured to provide the individual with a fitness forecast using the route. Such a fitness forecast tells individual at what time there dates his or her fitness level will achieve certain standards presuming that the route is followed.

Figure 5:
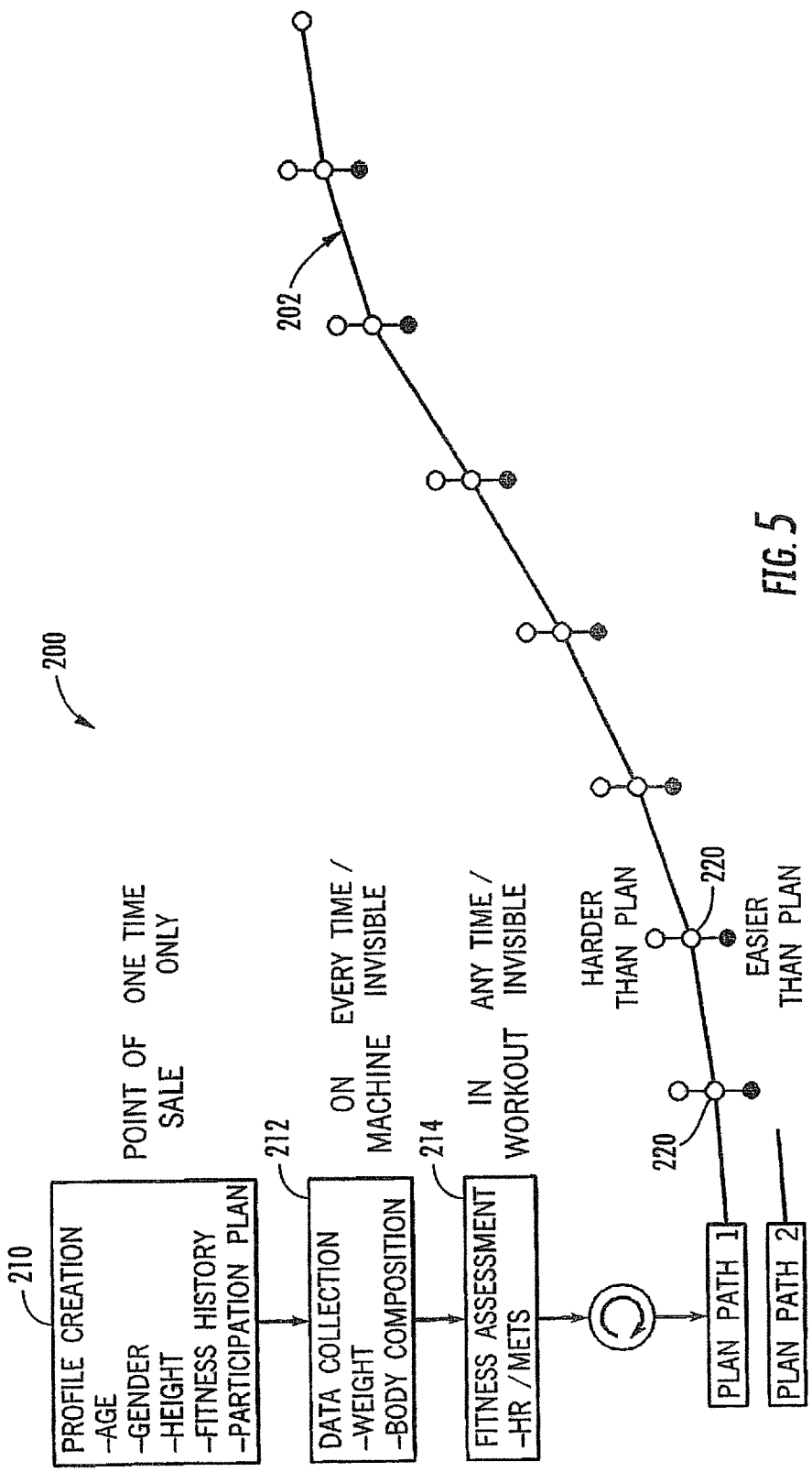
FIG. 5 is a flow diagram of a method used by the system of FIG. 1 to generate the list rated exercise route.

FIG. 5 illustrates one example process 200 by which exercise guidance system 10 creates and adjusts an exercise route 202. As indicated by step 210, system 10 initially may create profile which includes such attributes as an individual's age, gender, height, fitness history and participation plan. Such information may be acquired from the person's physician or health care provider.

As indicated by step 212, system 10 further proceeds with data collection regarding a person's weight and body composition. This data collection may be achieved using input 16 or may be achieved using various sensors on an exercise device. As indicated by step 214, during a workout, system 10 obtained additional fitness assessment information such as a person's heart rate or metabolic equivalent (Mets). Based upon all of the collected data, system 10 generates the illustrated exercise route 202.

Exercise route 202 (also referred to as a "plan path") includes a multitude of individual workouts 220 (illustrated as nodes). After each workout, or after a predefined minimum number of workouts (to reduce continual adjustment of an exercise route), system 10 adjusts the exercise route. Such adjustment may be such that the excise route is more difficult or alternatively is easier.

The exercise route 202 may be adjusted based upon other factors as well. For example, if controller 20 identifies a trend or pattern of the individual cutting short the duration of each workout, controller 20 may automatically adjust the duration of each workout to better accommodate the individuals' limited time or time demands. In one embodiment, controller 20 may provide the individual with an option of either delaying or prolonging the date for his or her fitness objectives being met or may request to increase the intensity or frequency of the shorter time workouts.

In addition to determining or identifying an exercise route for achieving one of more fitness objectives or goals and automatically adjusting the route based upon a comparison of exercise results or exercise metrics with the exercise route, user adherence and unplanned or planned user events, input 16, display 18 and controller 20 (serving as a computing device) also provide a person or individual exercising with enhanced flexibility or an increased range of options along the route for pursuing fitness objectives or goals. Rather than dictating to the person what individual exercise devices must be used and what specific settings or parameters (resistance level, speed, and the like) must be used for a particular workout 220 of the route 202 (shown in FIG. 5), controller 20 provides or displays to the person about to exercise different options for satisfying the requirements of the workout 220 and the requirements of route 202 from which the person may select. The displayed exercise options are interchangeable for a same portion of the workout 220. For example, a person about to exercise during one of workouts 220 (shown in FIG. 5) may be provided with different choices for the workout. He or she may choose from amongst different workout options potentially having different exercise options or the same exercise options with different settings or parameters associated with each option.

For purposes of this disclosure, the term "exercise option" means a type of exercise such as exercising on one or more different exercise devices, such as exercise devices 112A and 112B, shown in FIGS. 2 and 3, respectively, or using other exercise machines or devices (stair stepper, cycling exercise device, adaptive motion exercise device and the like) and/or exercising by using free weights, terrestrial motion, yoga, aerobics or other exercise activities which may or may not utilize exercise machines per se. For purposes of this disclosure, the term "terrestrial motion" means running, bicycling, climbing, jogging or walking independent of an stationary exercise machine such as a treadmill, elliptical machine, stationary cycling device, stair stepper, or adaptive motion exercise machine. Adaptive motion exercise machines are those machines that provide different instantaneously changeable paths of motion depending upon force applied to the machine by the person exercising. Exercise metrics or results from such terrestrial motion or other exercise activities independent of exercise machines may be provided to controller 20 by either direct input from a person exercising through input 16 (shown in FIG. 1) or downloads of metrics obtained and stored by other sensing devices carried by the person exercising or traveling bicycle during exercise such as blood pressure sensing devices or distance sensing devices such as global positioning sensing watches or shoe inserts and the like.

Each of the exercise options may have the same or different exercise option parameters. For purposes of this disclosure, an exercise option "parameter" means the adjustable or variable settings and time duration of exercise with the particular exercise option. Examples of parameters include, but not limited to, resistance settings, motion paths, movement heights, travel distances, acceleration rates, speed rates, distances and time durations. Parameters for an elliptical exercise device (a first exercise option) may include resistance, speed and a time duration for each of the different resistance and speed portions. Parameters for an adaptive motion exercise device may include resistance, speed, one or more selectable motion paths (paths through which a person's feet or arms move while in engagement with the device), overall duration and duration for each different chosen resistance, speed or path. Parameters for terrestrial motion, such as a run (a second exercise option), may include one or more of speed, distance or elevation change.

To facilitate the identification of workout options for a particular workout 220 along route 202 (shown in FIG. 5) that may be selectively interchanged while not substantially impacting the overall route 202 for achieving the person's exercise or fitness objectives, controller 20 defines each workout 220 or portions of each workout 220 in terms at least partially based on universal exercise measurement metrics such as metabolic equivalents (also known as METS). Because route 202 and its individual workouts 220 are defined by controller 20 using a common denominator of a metabolic equivalent (METS), multiple exercise options and multiple different exercise option parameters may be easily identified as being interchangeable for a workout 220 or portions of a workout 220. In some embodiments, workout 220 of route 202 may additionally be defined based upon a level of relative personal or perceived exertion which is based upon metabolic equivalents and an oxygen processing efficiency of the person, $VO_2$ max. In one embodiment, relative perceived exertion is defined by $1/(VO_2 max*MET)$.

In addition, during a workout, controller 20 converts exercise metrics or exercise results data from multiple different exercise options (types of exercise devices or types of terrestrial motion) to the common denominator of metabolic equivalents prior to adjusting route 202 for subsequent future workouts 220. Controller 20 then adjusts route 202 of workouts 220 using the metabolic equivalents from the exercise results of each of the different exercise options are exercise devices. As a result, exercise results from different exercise options or different exercise devices may be more easily integrated into adjustments to the plan or route 202.

FIG. 6 illustrates one example of the display of different workout options for a workout 220 (shown in FIG. 5) by display 18 under the direction of controller 20 (shown in FIG. 1). FIG. 6 illustrates the presentation of 10 different workout options row 300-318 by display 18 (shown in FIG. 1). Each of the options 300-318 are interchangeable and are selectable by a person for workout 220. Options 300-304 correspond to a first exercise option $O_1$, wherein each option 300-304 has different parameters P for the particular exercise option. Options 306-308 correspond to a second exercise option $O_2$ different than the first exercise option $O_1$. Each of Options 304-306 has different parameters P. Options 310 and 312 correspond to a second exercise option $O_3$ different than the first exercise option $O_1$ and the second exercise option $O_2$. Each of Options 310 and 312 has different parameters P. Options 314-318 have different combinations of multiple exercise options $O_1$-$O_4$. In one example, option O1 may comprise exercise on an elliptical machine. Option $O_2$ may comprise exercise on a treadmill. Option $O_3$ may comprise a terrestrial motion exercise. Option $O_3$ may comprise exercise on an adaptive motion machine In other embodiments Options $O_1$-$O_4$ may comprise other forms of exercise. In other embodiments, the workout options may include greater than free exercise options. In other embodiments, controller 20 may identify and cause display 18 to present a greater or fewer of such workout options.

In addition to presenting interchangeable workout options that may be selected by a person while still allowing a person to progress towards his or her fitness objectives, controller 20 may also determine and present workout options best suited to the available time a person has for the particular workout 220. Due to the hustle and bustle of present-day life, many individuals they often arrive late to or need to depart early from a workout facility. The initially planned and anticipated workouts cannot be performed in the reduced amount of time that they have available. As a result, the workouts are cut short and the person fails to stay on track with route 202.

However, controller 20 takes into account the persons available time for a particular workout and determines particular workout options that may be performed in a shorter period of time while still allowing a person to stay on track with route 202. For example, controller 20 may identify different workout options using different, possibly more intense, exercise options or may adjust the parameters for the same previous exercise option so as to be more intense source to accommodate the shorter available time. In other circumstances where the person may have additional time than previously anticipated, controller 20 may identify workout options having different exercise options or the same exercise option with different parameters. As a result, controller 20 facilitates an optimal use of available time for the person exercising.

According to one embodiment, controller 20 may request or otherwise obtain a universal time value which defines the available amount of time for the workout. For purposes of this disclosure, a "universal time" means a time value based upon rotation of the earth and is not a time duration or period. Examples of universal time include 11:00 PM CST, 1:25 AM PST and the like. In one embodiment, controller 20 may prompt a person about to exercise for universal time comprising a universal time for completing the workout, a universal time for leaving a workout facility or a universal time for arriving at a location remote from a workout facility. For purposes of this disclosure, a "workout facility" is a location where an exercise activity takes place such as a gym, health club or a person's residence. Based on this input universal time and the current universal time, controller 20 determines the available time for the workout and using this available time determines or identifies workout options that meet the person's objectives for the particular workout 220 (as prescribed by route 202) in the persons available time.

In another embodiment, instead of prompting the person about exercise for the universal time value to be used to determine the available time, controller 20 may alternatively consult a user profile for this universal time. For example, a person may create a universal profile, stored in memory 24, which provides the person's itinerary or schedule for the particular day or multiple days. Instead of being stored in memory 24, controller 20 may alternatively access and obtain this universal time in a wired or wireless fashion from an external scheduling device of the person such as the person's personal data assistant, computer calendar or the like. When the person indicates his or her presence through input 16 or through other presence sensors (either at the workout facility or at a particular exercise device), controller 20 may automatically consult memory 24 or the external scheduling device to obtain the universal time at which the person is scheduled to complete the workout, a universal time at which the person is scheduled for leaving the workout facility or a universal time at which the person is scheduled for arriving at a location remote from a workout facility. The available time is then determined by controller 20 using the future universal time and the present universal time, wherein controller 20 suggests and presents workout options based upon the determined available time.

In one embodiment, controller 20 may base its determination of the available time upon additional factors input by the person using input 16, obtained from a person or user profile in memory 24 or another memory, or obtained from an external scheduling device. For example, in circumstances where the universal time is the time for leaving the workout facility rather than merely completing a workout, controller 20 may base its determination of additional time using a persons hygiene time allotment (the expected time required for a person to cool down, shower and change clothes following a workout) as stored in the personal profile or contained in an external data source.

In circumstances where the universal time is a time for arriving at a remote location, controller 20 may base its determination upon an estimated time for traveling from the workout facility to a particular remote location. In one embodiment, controller 20 may consult a user profile including a plurality of locations remote from a workout facility that the person exercising frequently travels to following a workout. For example, the user profile may include addresses for a person's home, place of work, a commercial site or other locations. Prior to the person beginning his or her workout, controller 20 may present the various potential remote locations, wherein the person may be prompted to select one of the locations in which he or she intends to travel after the workout. Using mapping or travel applications or software (either stored in memory 24 or through an Internet source such as MAPQUEST mapping service), controller 20 may determine an estimated time for travel from the workout facility to the selected remote location. In some embodiments, controller 20 may additionally consult sources of traffic data to further adjust the estimated amount of travel time required and current or expected traffic conditions. In other embodiment, the person may input an estimated travel time from the workout location to one or more remote locations, wherein such travel times are stored in memory 24 or other memory locations.

By way of example, in one embodiment, a person may arrive at a workout facility at 5:00 PM and indicate that he or she must complete the workout by 5:50 PM. Controller 20 determines that the person has 50 minutes of available workout and would present workout options that fit within the 50 minutes of available time. In another embodiment, a person may arrive at a workout facility at 5:00 PM and indicate that he or she must leave the workout facility by 6:15 PM. After consulting the user profile indicating that the person usually requires 10 minutes for personal hygiene time following a workout, controller 20 determines that the person has 55 minutes of available time for the workout and presents workout options that fit within the 55 minutes of available time.

In yet another embodiment, the person may arrive at a workout facility at 5:00 PM and indicate that he or she must return home by 7:00 PM. After consulting the user profile indicating that the person usually requires 10 minutes for personal hygiene time following a workout and that the travel time between the workout facility or location and the persons residence is 45 minutes given the expected traffic conditions, controller 20 determines that the person has 65 minutes of available time for the workout and presents workout options that fit within the 65 minutes of available time. These are but a few examples of how controller 20 may facilitate optimal use of the person's available time for staying on track with his or her exercise objectives for a particular workout while also reducing the person's worry and stress about meeting appointments.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An apparatus comprising:
   a non-transitory computer-readable medium containing code configured to direct a processing unit to:
   receive a fitness objective of a person;
   identify and store an exercise route of workouts for achieving the fitness objective, each workout defined in terms at least partially based on metabolic equivalents; and
   a display a plurality of different exercise options and their associated parameters, the plurality of different exercise options being interchangeable for a same portion of a workout of the exercise route and being selectable by the person, the workout parameters for each of the plurality of exercise options being based at least partially upon a metabolic equivalent of the parameters for each of the plurality of exercise options.

2. The apparatus of claim 1, wherein the code is further configured to direct the processor to:
   receive first exercise results data from a first type of exercise device;
   convert the first exercise results data to a first metabolic equivalent;
   receive second exercise results data from a second type of exercise device different than the first type of exercise device;
   convert the second exercise results data to a second metabolic equivalent; and
   adjust the route of workouts using the first metabolic equivalent and the second metabolic equivalent.

3. The apparatus of claim 2, wherein the first type of exercise device and the second type of exercise device are selected from a group of exercise devices consisting of: an elliptical exercise device, a treadmill, a stair stepper, a cycling exercise device and an adaptive motion exercise device.

4. The apparatus of claim 1, wherein the plurality of exercise options includes terrestrial motion and exercising on an exercise device.

5. The apparatus of claim 1, wherein which of the plurality of exercise options are displayed is based upon available time for a workout.

6. The apparatus of claim 5, wherein the code is further configured to direct the processor to:
   receive a universal completion time;
   determine the available time for the workout using a current universal time and the received universal completion time.

7. The apparatus of claim 1, wherein the parameters associated with the exercise options that are displayed are based upon available time for a workout.

8. The apparatus of claim 7, wherein the code is further configured to direct the processor to:
receive a universal time for completing a workout;
determine the available time for the workout using a current universal time and the received universal time for completing the workout.

9. The apparatus claim 8, wherein the code is further configured to direct the processor to:
receive a universal time for leaving a workout facility;
determine the available time for the workout using a current universal time and the received universal time for completing the workout.

10. The apparatus of claim 9, wherein the code is further configured to direct the processor to:
store a user profile including a hygiene time allotment, wherein the available time is determined using the hygiene time allotment.

11. The apparatus of claim 8, wherein the code is further configured to direct the processor to:
receive a universal time for arriving at a location remote from a workout facility;
determine the available time for the workout using a current universal time and the universal time for arriving at a location remote from a workout facility.

12. The apparatus of claim 10, wherein the code is further configured to direct the processor to:
store a user profile including a plurality of locations remote from a workout facility; and
receive a selection of one of the plurality of locations, wherein the location comprises the selection.

13. The apparatus of claim 7, wherein the code is further configured to direct the processor to:
display a plurality of workout options, each of the plurality of workout options having a different combination of different exercise options and/or different associated parameters, wherein the different options that are displayed are based upon the available time for the workout.

14. The apparatus of claim 1, wherein each workout is defined in terms at least partially based on relative perceived exertion.

15. The apparatus of claim 1, wherein each of the displayed plurality of different exercise options along with their associated parameters are interchangeable for the same portion of the workout while still satisfying requirements of the workout.

16. The apparatus of claim 1, wherein the plurality of exercise options that are interchangeable and that are displayed for selection comprises a first exercise option on an exercise device and a second exercise option selected from a group of exercise options consisting of: free weights, yoga, aerobics, running, bicycling, climbing, jogging and walking, each of which is independent of a stationary exercise machine.

17. The apparatus of claim 16, wherein the second exercise options are displayed for selection prior to the person completing the first exercise option.

18. The apparatus of claim 1 comprising determining an equivalency of each of the exercise options being displayed, and wherein the equivalency is based upon the metabolic equivalents and a determined oxygen processing efficiency of the person.

19. The apparatus of claim 1 further comprising determining, with the computing device, and available time for workout, wherein which of the plurality of exercise options are displayed is based upon the determined available time for the workout.

20. The apparatus of claim 19, wherein the determining of the available time for the workout is based upon an estimated time for personal hygiene following the workout.

21. The apparatus of claim 19, wherein the determining of the available time for workout is based upon an estimated travel time for the person to travel to and/or from a workout facility for the workout.

22. An exercise guidance system comprising:
a first exercise device of a first type;
a second exercise device of a second type different than the first type;
a display;
a computer readable program configured to:
receive a fitness objective for an individual;
identify and store an exercise route of workouts for achieving the fitness objective, each workout defined in terms at least partially based on metabolic equivalents;
display a plurality of different exercise options and their associated parameters, the plurality of different exercise options being interchangeable for a same portion of a workout of the exercise route and being selectable by the person; the workout parameters for each of the plurality of exercise options being based at least partially upon a metabolic equivalent of the parameters for each of the plurality of exercise options, wherein the plurality of exercise options include exercise using the first exercise device and exercise using the second exercise device.

23. The exercise guidance system of claim 22, wherein the computer readable program is configured to:
receive first exercise results data from a first type of exercise device;
convert the first exercise results data to a first metabolic equivalent;
receive second exercise results data from a second type of exercise device different than the first type of exercise device;
convert the second exercise results data to a second metabolic equivalent; and
adjusting the route of workouts using the first metabolic equivalent and the second metabolic equivalent.

24. The exercise guidance system of claim 23, wherein the first type of exercise device and the second type of exercise device are selected from a group of exercise devices consisting of: an elliptical exercise device, a treadmill, a stair stepper, a cycling exercise device and an adaptive motion exercise device.

25. The exercise guidance system of claim 22, wherein the plurality of exercise options includes terrestial running and exercising on an exercise device.

26. The exercise guidance system of claim 22, wherein which of the plurality of exercise options are displayed is based upon available time for a workout.

* * * * *